US008101599B2

(12) United States Patent
Shetty et al.

(10) Patent No.: US 8,101,599 B2
(45) Date of Patent: Jan. 24, 2012

(54) PHARMACEUTICAL COMPOSITION CONTAINING ANTI-HYPERTENSIVE AGENTS

(75) Inventors: Suraj S Shetty, Far Hills, NJ (US); Randy L Webb, Flemington, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/338,066

(22) Filed: Dec. 18, 2008

(65) Prior Publication Data

US 2009/0099241 A1   Apr. 16, 2009

Related U.S. Application Data

(63) Continuation of application No. 10/514,682, filed as application No. PCT/EP03/05180 on May 16, 2003, now abandoned.

(60) Provisional application No. 60/381,547, filed on May 17, 2002.

(51) Int. Cl.
*A61K 31/54* (2006.01)
*A61K 31/53* (2006.01)
*A01N 43/66* (2006.01)
*A01N 43/40* (2006.01)
*A61K 31/44* (2006.01)

(52) U.S. Cl. ............ 514/222.8; 514/241; 514/356; 514/183

(58) Field of Classification Search ............ 514/183
See application file for complete search history.

(56) References Cited

U.S. PATENT DOCUMENTS

| 5,202,322 | A | 4/1993 | Allen et al. ............ 514/228.2 |
| 5,256,667 | A | 10/1993 | Alles et al. |
| 5,260,325 | A | 11/1993 | Markwalder et al. |
| 5,264,447 | A | 11/1993 | Ohtawa |
| 5,266,583 | A | 11/1993 | Ohtawa |
| 5,395,728 | A | 3/1995 | Jacovich et al. ............ 430/192 |
| 5,399,578 | A | 3/1995 | Bühlmayer et al. |
| 5,449,682 | A | 9/1995 | Greenlee et al. |
| 5,492,904 | A | 2/1996 | Wong |
| 5,656,650 | A | 8/1997 | Weinstock ............ 514/396 |
| 5,721,263 | A | 2/1998 | Inada et al. ............ 514/381 |
| 5,889,020 | A | 3/1999 | Huxley et al. ............ 514/303 |
| 5,962,500 | A | 10/1999 | Eide et al. ............ 514/410 |
| 5,965,592 | A | 10/1999 | Buhlmayer et al. |
| 5,985,915 | A | 11/1999 | Frangin et al. ............ 514/469 |
| 5,994,348 | A | 11/1999 | Ku et al. ............ 514/223.5 |
| 6,204,281 | B1 | 3/2001 | Webb et al. ............ 514/381 |
| 6,294,197 | B1 | 9/2001 | Wagner et al. ............ 424/465 |
| 6,395,728 | B2 | 5/2002 | Webb et al. ............ 514/212.04 |
| 2001/0049384 | A1 | 12/2001 | Webb |
| 2002/0107236 | A1 | 8/2002 | Sahota ............ 514/211.07 |

FOREIGN PATENT DOCUMENTS

| CA | 2 331 414 A1 | 11/1999 |
| CN | 1301545 A | 7/2001 |
| DE | 198 20 151 | 5/1998 |
| DE | 100 04 651 | 2/2000 |
| DE | 10004651 A1 | 8/2001 |
| EP | 0 244 944 | 11/1987 |
| EP | 0 400 835 | 12/1990 |
| EP | 0502314 A1 | 9/1992 |
| EP | 0 628 313 | 12/1994 |
| EP | 1 507 529 B1 | 2/2005 |
| WO | WO 92/10097 | 6/1992 |
| WO | 92/20342 | 11/1992 |
| WO | WO 92/20342 | 11/1992 |
| WO | 93/17682 | 9/1993 |
| WO | WO 95/21609 | 8/1995 |
| WO | 95/24901 | 9/1995 |
| WO | 97/36874 | 10/1997 |
| WO | 97/49394 | 12/1997 |
| WO | 97/49394 A2 | 12/1997 |
| WO | 98/46270 | 10/1998 |
| WO | WO 99/56734 | 11/1999 |
| WO | 00/02543 | 1/2000 |
| WO | 00/38676 A1 | 7/2000 |
| WO | 00/44378 A1 | 8/2000 |
| WO | WO 01/56609 | 8/2001 |
| WO | WO 01/56609 A1 | 8/2001 |
| WO | 02/06253 A1 | 1/2002 |
| WO | 02/43807 A2 | 6/2002 |
| WO | 2007/022113 A2 | 2/2007 |
| WO | 2007/022113 | 3/2007 |

OTHER PUBLICATIONS

Fogari et al., Effects of four angiotensin II-receptor antagonists on fibrinolysis in postmenopausal women with hypertension, 2001, Current Therapeutic Research, vol. 62, No. 1, pp. 68-78.*
Corea et al,"Valsartan, a new angiotensin II antagonist for the treatment of essential hypertension: A comparative study of the efficacy and safety against amlodipine," Clinical Pharmacology & Therapeutics, vol. 60, No. 3, pp. 341-346 (1996).
Prasad et al., "A Pharmacokinetic Interaction Between an Angiotensin II Receptor Blocker (Valsartan) and a Calcium Channel Blocker (Amlodipine)," American Journal of Hypertension, vol. 10, No. 4, Part 2 [Abstract D12] (1997).
Excerpt of NDA20665 from the US drug product containing Valsartan.
Fujimura et al., "Antihypertensive effect of a combination of valsartan and hydrochlorothiazide, nifedipine or propranolol in spontaneously hypertensive rats," Jpn. Pharmacol. Ther., vol. 23, No. 12, pp. 87-93, [Abstract D3] (1995).
Tarif et al., "Preservation of renal function: the spectrum of effects by calcium-channel blockers," Nephrol. Dial. Transplant., vol. 12, pp. 2244-2250 (1997).
Patient leaflet of Norvasc.
Fujimura et al., "Antihypertensive effect of a combination of valsartan and hydrochlorothiazide, nifedipine or propranolol in spontaneously hypertensive rats," Chemical Abstracts, vol. 17, No. 124, abstract No. 220073 (1996).
Hoelscher et al., "Antihypertensive therapy and Progression of Diabetic Renal Disease," Journal of Cardiovascular Pharmacology, vol. 23, Suppl. 1, pp. S34-S38 (1994).

(Continued)

*Primary Examiner* — Meghan Finn
(74) *Attorney, Agent, or Firm* — Joseph T. Majka

(57) ABSTRACT

The present invention relates to a combination of organic compounds, a pharmaceutical composition and a kit of parts comprising said combination of organic compounds and to a method of treatment or prevention of certain conditions or diseases.

30 Claims, No Drawings

OTHER PUBLICATIONS

Cao et at., "Angiotensin converting enzyme inhibition and calcium antagonism attenuate streptozotocin-diabetes-associated mesenteric vascular hypertrophy independently of their hypotensive action," Journal of Hypertension, vol. 16, No. 6, pp. 793-799 (1998).
McInnes, "Clinical Advantage of Valsartan," Cardiology, vol. 91, Suppl. 1, pp. 14-18 (1999).
Bakris et al., "Clinical Efficacy and Safety Profiles of AT1 Receptor Antagonists," Cardiovascular Reviews and Reports, vol. 20, No. 2, pp. 77-100 (1999).
Product Information Sheet; Exforge film coated tablets Feb. 2007.
Faulhaber et al., "Effect of Valsartan on Renal function in Patients with Hypertension and Stable Renal Insufficiency," Current Therapeutic Research, vol. 60, No. 3, pp. 170-183 (1999).
Makrilakis et al., "New Therapeutic Approaches to Achieve the Desired Blood Pressure Goal," Cardivascular Reviews and Reports, vol. 18, pp. 10-16 (1997).
Monthly Index of Medical Specialities, May 1998, pp. 46, 58, 70-72, 74 and 376.
Definition of 'ventricular hypertrophy', Dorland's Illustrated Medical Dictionary, 28th ed.,1994.
Monthly Index of Medical Specialities, Aug. 1996, pp. 46,64 and 323.
ABPI Compendium of Data Sheets and Summaries of Product Characteristics 1996-1997, p. 750.
Allen, T.J . et al., "Effect of Combination Therapy (Ang II Antagonist, Valsartan and a Calcium Channel Blocker) in a Hypertensive Model of Diabetic Nephropathy," Nephrology, vol. 5, No. 3, pp. A70-A70 (2000).
Remuzzi, A. et al., "Prevention of Renal Injury in Diabetic MWF Rats by Angiotensin II Antagonism," Experimental Nephrology, vol. 6, pp. 28-38 (1998).
Allen, T.J. et al., "Role of Angiotensin II and Bradykinin in Experimental Diabetic Nephropathy—Functional and Structural Studies," Diabetes, vol. 46, pp. pp. 1612-1618 (1997).
Susic, D. et al., "Nephroprotective effect of antihypertensive drugs in essential hypertension," Journal of Hypertension, vol. 16, pp. 555-567 (1998).
Bakris et al., "Effects of an ACE inhibitor combined with a calcium channel blocker on progression of diabetic nephropathy," J. Hum. Hypertens., vol. 11, pp. 35-38 (1997).
Widimsky et al. Vnetr. Lik., vol. 44, pp. 326-331, [abstract] (1998).
The Sixth Report of the Joint National Committee on Prevention, Dectection, Evaluation, and Treatment of High Blood Pressure (1997) Arch Intern Med. 157: 2413-2446.
Australian Family Physician 27:914-921 (1998).
Pharmaceutical Dosage Forms: Tablets Vol. 1, $2^{nd}$ edition (1989) Lieberman, H.A. et al., (ed.), Marcel Dekker, New York, pp. 108-110, 173-177, 226, 232, 234, 235, 239, 243, 245, 246.
Rernington's Pharmaceutical Sciences, 18th edition (1990) Gennaro, A.E. et. al. (ed.), Mack, Easton, pp. 1633-1637.
Belcher et al. "Candesartan cilexetil: safety and tolerability in healthy volunteers and patients with hypertension," Journal of Human Hypertension, vol. 11(Suppl.2), pp. S85 to S89 (1997).
Farsang et al., "Antihypertensive Effects and Tolerability of Candesartan Cilexetil, Amlodipine, and Their Combination," American Journal of Hypertension (1997), vol. 10. No. 4, p. 8OA, [abstract HI3] ((1997).
Cifkova et al., "Valsartan and atenolol in Patients with Severe Essential Hypertension," Journal of Human Hypertension, vol. 12, p. 563-567 (1998).
Marketing information concerning amlodipine besylate tablets ("Norvasc®") from Pfizer, published in Jun. 1996.
Hypertension, vol. 22, pp 392-403 (1993).
Wofford, "History of Fixed-Dose Combination Therapy for Hypertension," Arch Intern Med, vol. 157, p. 1044 (1997).
Waeber et al., "Combination Antihypertensive Therapy: Does It Have a Role in Rational Therapy?" American Journal of Hypertension, vol. 10, pp. 131S-137S (1997).
Epstein et al., "Newer Approaches to Antihypertensive Therapy," Arch Intern Med, vol. 156, pp. 1969-1978 (1996).

Sever, "Clinical profile of the novel angiotensin II type I blocker candesartan cilexetil," Journal of Hypertension, vol. 15 (Supl.6), pp. S9-S12 (1997).
MacGregor et al., "The Efficacy of Candesartan: An Angiotensin Type I Receptor Antagonist alone or in combination with amlodipine or in Combination with Amlodipine and Hydrochlorothiazide in Patients with Moderate-to-Severe Essential Hypertension," ASH XII Abstracts, No. D29, American Journal of Hypertension, vol. 10, No. 4, part 2 [Abstract] (1997).
Grossman et al., "Hemodynamic and Humoral Effects of the Angiotensin II Antagonist Losartan in Essential Hypertension," American Journal of Hypertension, vol. 7, pp. 1041-1044 (1994).
Tabrizchi et al., "The effects of losartan and captopril on vasopressor actions of cirazoline in the absence and presence of SZL-49 and nifedipine," Journal of Cardiovascular Pharmacology, vol. 26, No. 1 (pp. 137-144 [Abstract] (1995).
Markham et al., "Valsartan: A review of its Pharmacology and Therapeutic Use in Essential Hypertension," Drugs, vol. 54, No. 2, pp. 299-311 (1997).
Bowlus et al., "A comparison of the antihypertensive effect of chlorthalidone and hydrochlorthiazide," Clinical Pharmacology & Therapeutics, vol. 5, pp. 708-711 (1964).
Dunlay et al., "Losartan potassium as initial therapy in patients with severe hypertension," Journal of Human Hypertension, vol. 9, pp. 861-867 (1995).
Whalen, "Definition of the effective dose of the converting-enzyme inhibitor benazepril," American Heart Journal, vol. 117, No. 3, pp. 728-734 (1989).
Internet abstract of the Federal Drug Administration, showing that the application of D13 was aproved on Mar. 6, 1998.
List of Valsartan approvals in different countries before Jul. 1998.
United States Food and Drug Administration, Center for Drug Evaluation and Research, application No. 20-364/S-007, Lotrel (benazepril HCl plus amlodipine besylate), Novartis Pharmaceuticals Corp. (1997).
Chobanian et al., "Seventh Report of the Joint National Committee on Prevention, Detection, Evaluation, and Treatment of High Blood Pressure," Hypertension, vol. 42, pp. 1206-1252 (2003).
Kearney et al., "Global burden of hypertension: analysis of worldwide data," Lancet, vol. 365, pp. 217-223 (2005).
1999 WHO—International Society of Hypertension Guidelines for the Management of Hypertension, Journal of Hypertension, vol. 17, pp. 151-183 (1999).
Cook et al., "Implications of Small Reductions in Diastolic Blood Pressure for Primary Prevention," Arch. Intern. Med., vol. 155, pp. 701-709 (1995).
Plosker et al., "Amlodipine/Valsartan Fixed-Dose Combination in Hypertension," Drugs, vol. 68, No. 3, pp. 373-381 (2008).
Chaplin et al., "Exforge: ARB/CCB combination for better hypertension control," Prescriber, vol. 18 (23-24), pp. 44-47 (2007).
Philipp et al., "Two Multicenter, 8-Week, Randomized, Double-Blind, Placebo-Controlled, Parallel-Group Studies Evaluating the Efficacy and Tolerability of Amlodipine and Valsartan in Combination and as Monotherapy in Adult Patients with Mild to Moderate Essential Hypertension," Clinical Therapeutics, vol. 29, No. 4, pp. 563-580 (2007).
Sinkiewicz et al., "Efficacy and tolerability of amlodipine/valsartan combination therapy in hypertensive patients not adequately controlled on valsartan monotherapy," Current Medical Research and Opinions, vol. 25, No. 2, pp. 315-324 (2009).
Webb et al., The chronic effects of valsartan with amlodipine on blood pressure and cardiac mass in spontaneously hypertensive rats (SHR). Abstracts. $18^{th}$ Scientific Meeting of the International Society of Hypertension, J. Hypertens (Supp 4) vol. 18, p. S80 (2000).
MacGregor, Antonios and He, "The Efficacy of Candesartan; an Angiotensin II Type I Receptor Antagonist Alone or in Combination With Amlodipine or in Combination With Amlodipine and Hydrochlorothiazide in Patients With Moderate-to-Severe Essential Hypertension", *Am J Hypertens*, vol. 10, No. 4, Part 2, p. 112A-D29 (1997).
MacGregor, "Efficacy of Candesartan Cilexetil Alone or in Combination With Amlodipine and Hydrochlorothiazide in Moderate-to-Severe Hypertension", *Hypertension*, vol. 36, No. 3, pp. 454-460 (2000).

Ohnishi et al., "Influence of the Angiotensin II Receptor Antagonist Losartan on Diuretic-induced Metabolic Effects in Elderly Hypertensive Patients: Comparison with a Calcium Channel Blocker", *Int J Clin Pharmacol Ther*, vol. 39, No. 10, pp. 417-422 (2001).

Oparil et al., "Efficacy, Tolerability, and Effects on Quality of Life of Losartan, Alone or With Hydrochlorothiazide, Versus Amlodipine, Alone or With Hydrochlorothiazide, in Patients With Essential Hypertension", *Clin Ther*, vol. 18, No. 4, pp. 608-625 (1996).

Oparil, Aurup, Snavely and Goldberg, "Efficacy and Safety of Losartan/Hydrochlorothiazide in Patients With Severe Hypertension", *Am J Cardiol*, vol. 87, No. 6, pp. 721-726 (2001).

Song et al., "Pharmacologic, Pharmacokinetic and Therapeutic Differences Among Angiotensin II Receptor Antagonsts", Pharmacotherapy 20(2); 130-139. (2000).

Palatini et al., "Trough:peak ratio and smoothness index in the evaluation of 24-h blood pressure control in hypertension: a comparative study between valsartan/hydrochlorothiazide combination and amlodipine", Eur. J. Clin. Pharmacol, 57: pp. 765-770 (2002).

Neutel, Jim, et al., "The Efficacy And Safety Of Telmisartan Compared to Enalapril in Patients With Severe Hypertension", Int. J Clin Pract, 1999, 55(3), 175-178.

Benz, Jr, et al., "Valsartan and hydrochlorothiazide in patients with essential hypertension. A multi dose, double-blind, placebo controlled trial comparing combination therapy with monotherapy", Journal of Human Hypertension, 1998, 12, 861-866.

Schmidt, A., et al., "Antihypertensive Effects of Valsartan/Hydrochlorothiazide Combination in Essential Hypertension", Blood Pressure, 2001, 10, 230-237.

Hall, W. Dallas, et al., "Efficacy and Tolerability of Valsartan in Combination with Hydrochlorothiazide in Essential Hypertension", 1998, Sep: 16(3): 203-210.

Palatini, P. et al., "A multicenter, randomized double-blind study of valsartan/hydrochlorothiazide combination versus amlodipine in patients with mild to moderate hypertension ", Journal of Hypertension 2001, 19:1691-1696.

Chrysant, S.G., "Fixed Low-Dose Drug Combination for the Treatment of Hypertension". Arch Fam Med, 1998; 7:370-376.

Wellington, K., et al., "Valsartan/Hydrochlorothiazide", Drugs 62(13): 1983-2005 (2002).

Gifford, R.W., "Drug Combinations as Rational Antihypertensive Therapy", Arch Intern Med, vol. 133, Jun. 1974.

Center for Drug Evaluation and Research; application No. 83-972, Approval Date Oct. 3, 1974 (as available via epoline file inspection of EP 96 115 146).

Angiotensin II Receptor Antagonists in Perspective, ed.: G. Mancia Martin Dunitz Ltd. 2000, ISBN 1-85317-731-8, p. 64 to 67.

Conlin, P.R., et al., "Angiotensin II Antagonists for Hypertension: Are There Differences in Efficacy?", AJH (American Journal of Hypertension) 2000; 13: 418-426.

Corea, L., et al., "Valsartan, a new angiotensin II antagonist for the treatment of essential hypertension: A comparative study of the efficacy and safety against amlodipine", Clinical Pharmacology &Therapeutics, 1996;60:341-346.

Prasad, P.P., et al., "A pharmacokinetic interaction between an angiotensin II receptor blocker (valsartan) and a calcium channel blocker (amlodipine)", American Journal of Hypertension, D12, Apr. 1997, vol. 10, No. 4, Part 2.

M. Witkowski et al., "Comparative study to assess the efficacy and safety of two calcium antagonists: amlodipine and nifedipine retard in patients with stable exertional angina and hypertension", Pnegla d lekarski 1996(5315); 324-328, Abstract Only Considered.

T. Saruta et al., "Efficacy and Safety of Amlodipine in Hypertensive Patients with Renal Dysfunction", Clin. Cardiol. vol. 17, Jun. 1994, 317-324, p. 322.

J. M. Detry et at., "Patient compliance and therapeutic coverage: comparison of amlodipine and slow release nifedipine in the treatment of hypertension", Eur J Clin Pharmacol(1995) 47:477-481.

Varrone et al., "A study of the efficacy and safety of amlodipine for the treatment of hypertension in general practice", Postgrad Med J (1991) 67 (Suppl 5), S28-S31, p. S29.

Glasser et al., "Safety and Efficacy of Amlodipine Added to Hydrochlorothiazide Therapy in Essential Hypertension", American Journal of Hypertension, Mar. 1989; 2(3 Pt 1):154-7.

Giles, Thomas D., et al., "Beyond the Usual Strategies for Blood Pressure Reduction: Therapeutic Considerations and Combination Therapies", The Journal of Clinical Hypertension, Dec. 2001; vol. III, No. VI; 346-352.

Calhoun et al. "Amlodipine/Valsartan/Hydrochlorothiazide Triple combination therapy in moderate/severe hypertension: Secondary analyses evaluating efficacy and safety", Adv. Ther., 26 (11) (2009).

Berkrot et al., "Novartis drugs fail to help high-risk patients" Internet article http://news.yahoo.com/s/nm/20100314/hl_mm/us_heart_novartis. (Mar. 16, 2010).

TSC Staff, Novartis' Diovan fails test: Report, The Street.com Drugs, Internet article www.thestreet.com/print/story/10702167 (Mar. 16, 2010).

Cortez, "Novartis heart, diabetes drugs fail to prevent disease in study", Bloomberg.com, Internet article http://www.bloomberg.com/apps/news?pid=20670001&sid=aD2Z6SAeCNvA (Mar. 16, 2010).

Novartis , "Novartis says Valsartan didn't reduce risk of cardiovascular events in Navigator study" RTTNews , Internet article http://www.rttnews.com/ArticlePrint.aspx?id=1239619 (Mar. 16, 2010).

Cortez, "Novartis heart, diabetes medications fall to prevent the diseases in trial", Feedcry Archive-Bloomberg, Internet Article http://www.feedcry.com/archive/aid/611627?utm_source=feedburner&utm_medium-feed (Mar. 16, 2010).

Loftus, "Novartis drugs fail in diabetes test", The Wall Street journal, (Mar. 14, 2010).

Barrie, William, "Cost-effective therapy for hypertension", West J. Med., 164, pp. 303-309 (1996).

Drug facts and comparisons®, 1997 Edition ($51^{st}$ Edition) (1997).

Ruschitzka et al. Is there a rationale for combining angiotensin-converting enzyme inhibitors and calcium antagonists in cardiovascular disease?, American Heart Journal, vol. 134, No. 2part II, pp. S31-S.

Campo, C., "Factors influencing the systolic blood pressure response to drug therapy", J. Clinical Hypertension, vol. 4, No. 1, pp. 35-40, (Jan. 2002).

Collins, R., et al., "Blood pressure, stroke and coronary hear disease", The Lancet, Part 2, vol. 335, pp. 827-838, (1990).

Waeber, B., et al., "Combination antihypertensive therapy: does it have a role in rational therapy?", American Journal of Hypertension, vol. 10, No. 7, pp. 131S-137S, (1997).

Bayliss, J., "Captopril in essential hypertension; contrasting effects of adding hydrocholorthiazide or propranolol", British Medical Journal, vol. 284, pp. 693-696, (Mar. 6, 1982).

Waeber, B., et al., "Combination of hydrochlorothiazide or benazepril with valsartan in hypertensive patients unresponsive to valsartan", J. Hypertension, vol. 19, No. 11, (Nov. 2001).

Bazil, M. et al., "Telemetric monitoring of cardiovascular parameters in conscious spontaneously hypertensive rats"., J. Cardiovascular Pharmacology, vol. 22, pp. 897-905, (1993).

Thibault, G., "Resistance artery mechanics, structure, and extracellular components in spontaneously hypertensive rats", Circulation, vol. 100, No, 22, pp. 2267-2275, (1999).

Intengan, H.D., et al., "Blood pressure and small arteries in DOCA-salt-treated genetically AVP-deficient rats: role of endothelin", Hypertension, vol. 34, No. 4, pp. 907-913 (1999).

Ceiler, H., J., et al, "Effect of chronic blockade of angiotensin II-receptor subtypes on aortic compliance in rates with myocardial infarction", J. Cardiovascular Pharmacology, vol. 31, No. 4, (1998).

Nagura, J. et al, "Protective effects of ME 3221 on hypertensive complications and lifespan in salt-loaded stroke-prone spontaneously hypertensive rats", Clinical and Experimental Pharmacology and Physiology, vol. 23., No. 3. pp. 229-235, (1996).

Nabata, H., et al., "Antihypertensive effects of a novel phenylpiperazine derivative, SBB-1534, on several hypertensive models of rats", Arch. Int. Pharmacodyn, vol. 277, No. 1, pp. 104-118, (1985).

Lacolley, P., et al., "Different effects of calcium antagonists on fluid filtration of large arteries and albumin permeability in spontaneously", Journal of Hypertension, vol. 16, No. 3, pp. 349-355, (1998).

Calhoun, D., et al., "Triple antihypertensive therapy with amlodipine, valsartan and hydrochlorothiazide: a randomized clinical trial", Hypertension, vol. 454, pp. 32-39, (2009).
Black, H., et al, "Triple fixed dose combination therapy: back to the past" Hypertension vol., 54, pp. 19-22, (2009).
Sixth Report of Joint Nat Committee on Prevention, Detection, Evaluation and Treatment of High Blook Pressure, NHI Pub 98-4080 (1997).
Deeks ED. Amlodipine/valsartan/hydrochlorothiazide: Fixed-dose combination in hypertension. Am J Cardiovasc Drugs 9(6):411-418 (2009).
Zappe et al.. Efficacy of valsartan/hydrochlorothiazide/ amlodipine triple combination in patients whose blood pressure was not controlled with dual combinations: the PROMPT extension study. J Hypertens; 27(suppl. 4):S121 (2009).
Braun N, Handrock R, Klebs S, et al. Triple combination of valsartan, amlodipine and HCTZ provides effective reduction of blood pressure in patients with hypertension not controlled by dual therapy with amlodipine plus valsartan or valsartan plus HCTZ. J Hypertens;27(suppl. 4):S272 (2009).
Flack JM, Calhoun DA, Satlin L, et al. Combination of angiotensin-receptor blocker, calcium-channel blocker and diuretic is safe and effective in the management of severe hypertension in blacks. J Clin Hypertens;10(5 Suppl A):A19 Abstract P-32. (2008).
Lacourciere Y, Glazer RD, Yen J, Calhoun DA. Twenty-four hour ambulatory BP control with amlodipine/valsartan/HCTZ triple combination therapy compared to dual therapy in patients with moderate to severe hypertension. J Hypertens; 27(suppl. 4):S271 (2009).
Lacourciere Y, Glazer RD, Crikelair N, Yen J, Calhoun D. Effect of baseline systolic blood pressure on response to triple combination amlodipine/valsartan/ hydrochlorothiazide in patients with moderate-to-severe hypertension. J Hypertens 27(Suppl.4):S119 (2009).
Calhoun DA, Glazer RD, Yen J, Lacourciere Y. Effect of age, gender, race and ethnicity on efficacy of amlodipine/valsartan/hydrochlorothiazide triple combination therapy in patients with moderate to severe hypertension. J Hypertens 27(Supple.4):S119 (2009).
Weycker D, Keskinaslan A, Levy D, Oster G. Effectiveness of add-on therapy with amlodipine in hypertensive patients receiving valsartan-hydrochlorothiazide. J Clin Hypertens;10(5 Suppl A):A37 Abstract P-74 (2008).
Smith TR, Glazer R, Koren MJ, et al. Long-term safety and efficacy of combination therapy with amlodipine and valsartan in hypertensive patients. J Clin Hypertens;10(5 Suppl A):A35. Abstract P-70 (2008).
Allemann Y, Fraile B, Lambert M, et al. Efficacy of the combination of amlodipine and valsartan in patients with hypertension uncontrolled with previous monotherapy: the Exforge in Failure After Single Therapy (EX-FAST) Study. J Clin Hypertens;10(3):185-194 (2008).
Flack JM, MD, MPH, Calhoun D, MD, Satlin L, et al. Initial combination therapy with amlodipine/valsartan is more effective than amlodipine monotherapy in black patients with stage 2 hypertension: the EX-STAND Study. J Hum Hypertens ; 23, 479-489 (2009).
Destro M, Luckow A, Samson M, et al. Efficacy and safety of amlodipine/valsartan compared with amlodipine monotherapy in patients with stage 2 hypertension: a randomized, double-blind, multicenter study: the Ex-EFFeCTS Study. J Am Soc Hypertens; 2(4):294-302 (2008).
Solomon SD, Verma A, Desai A, et al. Effect of Intensive versus Standard Blood Pressure Lowering on Diastolic Function in Patients with Uncontrolled Hypertension and Diastolic Dysfunction. Hypertens; 55:241-248 (2010).
Hassanein A, Desai A, Verma A, et al. exceed: Exforge®-intensive control of hypertension to evaluate efficacy in diastolic dysfunction: study rationale, design, and participant characteristics. Ther Adv Cardiovasc Dis; 3(6):429-439 (2009).
Braun N, Ulmer H-J, Ansari A, Handrock R, Klebs S. Efficacy and safety of the single pill combination of amlodipine 10mg plus valsartan 160mg in hypertensive patients not controlled by amlodipine 10mg plus olmesartan 20mg in free combination. Curr Med Res Opin; 25(2):412-430 (2009).

Zappe D, Papst CC, Ferber P; prompt Investigators. Randomized study to compare valsartan +/- HCTZ versus amlodipine +/- HCTZ strategies to maximize blood pressure control. Vasc Health Risk Manag.; 5:883-92. (2009).
Schweizer J, Hilsmann U, Neumann G, Handrock R, Klebs S. Efficacy and safety of valsartan 160/HCTZ 25 mg in fixed combination in hypertensive patients not controlled by candesartan 32 mg plus HCTZ 25 mg in free combination. Curr Med Res Opin; 23(11):2877-85 (2007).
White WB, Calhoun DA, Samuel R, et al. Improving BP control with fixed-dose ARB -diuretic therapy-findings from Valdictate study. J Clin Hypertens; 10(6):450-458 (2008).
American Journal of Hypertension, Twelfth Scientific Meeting, May 27 to 31, 1997, vol. 10, No. 4, part 2 Apr. 1997).
Novartis Press Release: Novartis announces efficacy data on new investigational high blook pressure therapies at the American Society of Hypertension annual meeting (May 17, 2006).
Reyes AJ, "Diuretics in the therapy of hypertension", J. Hum. Hypertens., 16 (Suppl.): S78-83 (Mar. 2002).
Muntwyler and Follath, "Calcium channel blockers in treatmen tof hypertension," Prog. Cardiovas. Dis., 44(3): 207-16 (2001).
Awan and Mason, "Direct selective blockade of the vascular angiotension II receptors in therapy for ypertension and severe congestive heart failure," Am. Heart J., 131(1): 177-85 (1996).
Close WJ et al, "Synthesis of Potential Diuretic Agents. I. Derivatives of 7-Sulfamyl-3,4-dihydro-1,2,4-benzothiadiazine 1,1-Dioxide", J. Am. Chem. Soc. 82, 1132-1135 (1960).
Berglund G et al, "Low Doses of hydrochlorothiazide in Hypertension Antihypertensive and Metabolic Effects", Eur. J. Clin. Pharmacol. 19, 177-182 (1976).
Notice of opposition to a European patent by opponent Krka, d. d., Novo mesto, reference No. 6309E29242 EPOP, dated Apr. 22, 2009.
Opposition Brief of Krka, d. d., Novo mesto, dated Jan. 21, 2010.
Communication of further notices of opposition pursuant to Rule 79(2) EPC to Michael Oliver Westendorp, dated Feb. 26, 2010.
Notice of opposition to a European patent by opponent Teva Pharmaceutical Industries Ltd., reference No. X039205EP KJG, dated Apr. 22, 2009.
Notice of opposition to a European patent by opponent Lupin Limited, reference No. RJW/FG6274120, dated Apr. 22, 2009.
Communication of further notices of opposition pursuant to Rule 79(2) EPC to Robert James Watson, dated Feb. 26, 2010.
Notice of opposition to a European patent by opponent Sanovel Ilac Sanayii ve Ticaret A.S., reference No. S1019 EP/OPP S3, dated Apr. 22, 2009.
Opposition Brief of Sanovel Ilac Sanayii ve Ticaret A.S., dated Jan. 21, 2010.
Communication of further notices of opposition pursuant to Rule 79(2) EPC to Alexa von Uexküll-Güldenband, dated Feb. 26, 2010.
Statement of Facts and Arguments by opponent, Teva Pharmaceutical Industries Ltd, received at EPO Jan. 21, 2010.
Notice of opposition to a European patent by opponent Teva Pharmaceutical Industries Ltd., reference No. X039205EP KJG, dated Apr. 22, 2009, signed by Tim Russell.
Communication of further notices of opposition pursuant to Rule 79(2) EPC to Kirk James Gallagher, dated Feb. 26, 2010.
Opposition Brief to Patent 223313 of Torrent Pharmaceuticals Ltd., dated Nov. 21, 2009.
India Patent 223313, "Combination of Organic Compounds" (complete specification), dated Oct. 17, 2004.
Reply Statement by Patentee, dated Nov. 17, 2004.
Further Evidence on Behalf of the Patentee by Dr. Henry R. Black, dated Jun. 24, 2010.
Meeting Minutes: Type B Meeting between NPC and FDA, subject: Diovan HCT plus amlodipine besylate Triple Combination Tablets IND 65.174 (Oct. 13, 2004).
DRAFT: Division of Cardio-Renal Drug Products "Proposed Guidelines for the c linical Evaluation of Antihypertensive Drugs" (May 9, 1988).
Center for Drug Evaluation and Research, Application No. 22-314, Summary Review (Apr. 25, 2009).

Jansson JH et al, "Tissue plasminogen activator and other risk factors as predictors of cardiovascular events in patients with severe angina pectoris", European Heart Journal, vol. 12, pp. 157-161 (1991).
Jansson JH et al, "von Willebrand factor in plasma: a novel risk factor for recurrent myocardial infarction and death", Br. Heart J, vol. 66, pp. 351-355 (1991).
Kirch W et al, "Comparison of angiotensin II receptor antagonists", European J of Clinical Investigation, vol. 31, pp. 698-706 (2001).
Mancia G, "Clinical Differences among Angiotensin II Receptor Antagonists", Blood Pressure, vol. 20, Suppl 2, pp. 19-24 (2001).
Center for Drug Evaluation and Research, Application No. 22-314, Summary Review (Apr. 25, 2009) [see same reference at P.C.].
Laragh's Lessons in Pathophysiology and clinical Pearls for Treating Hypertension, American J Hypertension, vol. 14, No. 6, pp. 491-503 (Jun. 2001).
Center for Drug Evaluation and Research, Application No. 20386/S018, Final Printed Labeling: Cozaar® (Jan. 28, 2000).
Center for Drug Evaluation and Research, Application No. 20838/S8, Final Printed Labeling: Atacand® (Jun. 14, 2000).
Center for Drug Evaluation and Research, Application No. 21-283, Final Printed Labeling: Diovan® (Jun. 2001).
Messerli FH et al, "Sublingual nifedipine for hypertensive emergencies" Letters to the Editor, The Lancet, vol. 338, p. 881 (Oct. 5, 1991).
Grossman E et al, "Should a Moratorium Be Placed on Sublingual Nifedipine Capsules given for Hypertensive Emergencies and Pseudoemergencies?", JAMA, vol. 276, No. 16, pp. 1328-1331 (Oct. 1996).
Ligtenberg G et al, "Reduction of Sympathetic Hyperactivity by Enalapril in Patients with Chronic Renal Failure", New England J Medicine, vol. 340, No. 17, pp. 1321-1328 (Apr. 29, 1999).
Memo, Dept Health & Human Svcs, subject: Approval of Exforge, 19 pages, Dec. 13, 2006.
Meeting Minutes: Pre-NDA Mtg between Novartis and FDA, subject: Diovan plus amlodipine besylate Combination Tablets IND 65,174, 5 pages, Apr. 14, 2005.
RHPM Overview, NDA 21-990. Exforge Tablets, 5 pages, Dec. 21, 2006.
Center for Drug Evaluation and Research, Application No. 21-990, Administrative & Correspondence Documents, Exforge 110 pages, Jan. 6, 2006.
English translation of Administrative Judgment from Beijing Higher People's Court, pp. 1-15, Sep. 19, 2010.
Proprietors Response to the Notices of Opposition, European Patent 1507529 B1, Nov. 8, 2010 (40 pages).
Rote List 1999, Hrsg.: Rote ListeB Service GmbH, items 17 168 and 27 150 [English translation of German text, submitted on Mar. 3, 2010].
Rote List 2001, Hrsg.: Rote ListB Service GmbH, items 17139, 17 187, 17 190, 27 157 [English translation of German text, submitted on Mar. 3, 2010].
Hagers Handbuch der pharmazeutischen Praxis, 5. Aufl. (1991), von Bruchhausen, F, et al., Hrsg.) Springer, Berlin, pp. 944-946, 971-974 [English translation of German text, submitted on Jun. 16, 2009].
Arzneiformenlehre, 4 Aufl. (1985) Wissenschaftliche Verlagsgesellschaft, Stuttgart, pp. 78-79, 82-83 [English translation of German text, submitted on Jun. 16, 2009].
Neutel, JM et al "Combination Therapy with Diuretics: An Evolution of Understanding" Am J Med 101(3A) pp. 61S-70S, Sep. 30, 1996.
Gradman AH et al, "Combination Therapy in Hypertension", The Journal of Clinical Hypertension, vol. 13, No. 3, pp. 146-154, Mar. 2011.
Canadian Family Physician, "Valsartan Just a second-line antihypertensive drug", vol. 45, pp. 2626-2628, Nov. 1999 [previously provided with form SB/08b on Oct. 21 2010 as "Annexture II"].
Epstein BJ, "Improving blood pressure control rates by optimizing combination antihypertensive therapy", Expert Opin. Pharmacother. 11(12), pp. 2011-2026, Aug. 2010.
Written Submission of Patentee in the matter of Indian patent No. 223313 (and post-grant opposition by Torrent Pharmaceuticals Limited) dated Apr. 6, 2011.
Unger, Thomas "Pharmacology of $AT_1$-receptor Blockers", Blood Pressure, vol. 10, Suppl 3, pp. 5-10 (2001).

Belz, Gustav G "Pharmacological Differences among Angiotensin II Receptor Antagonists", Blood Pressure, vol. 10, Suppl 2, pp. 13-18 (2001).
Brunner, Hans R "The New Angiotensin II Receptor Antagonist, lrbesartan", Am J Hypertens, vol. 10, pp. 311S-317S (1997).
Decision of pre-grant opposition against IPA 339/MUMNP/2006, dated Dec. 30, 2010.
Board of appeal of EPO T0686/91-33.1, dated Jun. 30, 1994.
Charm Trial Press Release, "Landmark heart failure study includes over 7500 participants—Charm study programme recruitment completed on schedule", Mar. 1, 2001 from website: http://www.eurekalert.org/pub_releases/2001-03/K-Lbfs-0103101.php, Accessed Jun. 8, 2011.
"Cardiovascular disease risk factors", World Heart Federation article from website: http://world-heart-federation.org/cardiovascular-health/cardiovascular-disease-risk-factors/#c481, downloaded on Jun. 8, 2011.
Capppuccio FP et al, "A Double-Blind Study of the Blood Pressure Lowering Effect of a Thiazide Diuretic in Hypertensive Patients Already on Nifedipine and a Beta-Blocker", J Hypertens, vol. 5, pp. 733-738 (1987).
Capppuccio FP et al, "A Double-Blind Crossover Study of the Effect of Concomitant Diuretic Therapy in Hypertensive Patients Treated with Amlodipine". Am J Hypertens, vol. 4, pp. 297-302 (1991).
Fogari R et al, "Effect of valsartan addition to amlodipine on ankle oedema and subcutaneous tissue pressure in hypertensive Patients", J Hum Hypertens, vol. 21, pp. 220-224 (2007).
Koh KK et al, "Angiotensin II type 1 receptor blockers reduce tissue factor activity and plasminogen activator inhibitor type-1 antigen in hypertensive patients: a randomized, double-blind, placebo-controlled study", Atherosclerosis, vol. 177, pp. 155-160 (2004).
Petition for Administrative Appeal by Novartis AG Patent Reexamination Board, People's Republic of China, dated Jan. 28, 2010.
Decision by Deputy Controller of Patents & Designs, India for Opposition by Torrent Pharmaceuticals to Patent 223313, dated May 25, 2011.
Chrysant SG, et al, "Antihypertensive effectiveness of amlodipine in combination with hydrochlorothiazide", American Journal of Hypertension, vol. 2, No. 7, pp. 537-541, Jul. 1989.
Langtry HG, et al, "Valsartan/Hydrochlorothiazide", Drugs, vol. 57, No. 5, pp. 751-755, May 1999.
Webster J, et al, "Once-Daily Amlodipine in the Treatmen tof Mild to Moderate Hypertension", Journal of Cardiovascular Pharmacology, vol. 12, Supplement 7, pp. S72-S75, 1988.
Thurmann, PA, "Valsartan: a novel angiotensin Type 1 receptor antagonist", Expert Opinion on Pharmacotherapy, vol. 1, No. 2, pp. 337-350, Jan. 2000.
Weber, MA, "Calcium Channel Antagonists in the Treatment of Hypertension", Cardiovascular Drugs, vol. 2, No. 6, pp. 415-431 (2002).
Excerpt of NDA20665 from the US drug product containing Valsartan, 2008.
Patient leaflet of Norvasc, 1995.
Auxiliary Request 1 to EPO, 1 claim, Sep. 8, 2011, 1 page.
Main Request to EPO, marked up copy of EP 1 407 429 B1, dated Sep. 8, 2011, 2 pages.
Opponent I (Lupin Limited) Rule 116 submissions to EPO, Sep. 6, 2011, 6 pages.
Opponent II (Teva Pharmaceutical Industries Ltd.) additional submission to EPO, Oct. 10, 2011, 3 pages.
Opponent II (Teva Pharmaceutical Industries Ltd.) Rule 116 submissions to EPO, Sep. 7, 2011, 15 pages.
Opponent IV (KRKA, d.d., Novo mesto) Rule 116 submissions to EPO, Aug. 4, 2011, 16 pages.
Patentees request for withdrawal to EPO, Oct. 7, 2011, 1 page.
Patentees Rule 1176 submissions to EPO, Sep. 8, 2011, 13 pages.
Citation in opposition procedure to EPO Sep. 6, 2011, Atacand™ Tablets package insert, issued May 1998, 9 pages.
Citation in opposition procedure to EPO Sep. 8, 2011, Norvasc® Tablets, Revised Apr. 2000, 4 pages.
MacGregor, G, Letter to the Editor: The St. George's 'Star' and 'Imploding Diamond', J Human Hypertension 13: 353-354 (1999).

Lloyd-Jones, DM et al, "Differential Impact of Systolic and Diastolic Blood Pressure Level on JNC-VI Staging", Hypertension 34:381-385 (1999).

Epstein, Franklin H., "Plasminogen-Activator Inhibitor type 1 and Coronary Artery Disease", NE J Medicine 342(24):1792-1801 (2000).

Van Zwleten, Peter A., "Comparative pharmacology of angiotensin II (AT1) receptor antagonists", Angiotensin II Receptor Antaoonists in Perspective, edited by Giuseppe Mancia, Martin Dunitz Ltd., 2000, pp. 21-38.

CDER approval of final labeling for Diovan™ Capsules, May 22, 2008, 5 pages.

Pantev, Emil et al, "Comparison of the antagonistic effects of different angiotensin II receptor blockers in human coronary arteries", European J of Heart Failure 4: 699-705 (2002).

* cited by examiner

PHARMACEUTICAL COMPOSITION CONTAINING ANTI-HYPERTENSIVE AGENTS

This application is a Continuation Application of Ser. No. 10/514,682, filed Jan. 7, 2005, which is a 371 of PCT/EP03/05180, filed May 16, 2003 and claims benefit of Provisional Application No. 60/381,547, filed May 17, 2002.

The present invention relates to a combination of organic compounds that are antihypertensive agents with complementary modes of action for eliciting blood pressure-lowering, and also for attenuating the varied pathological sequelae of hypertension and several other cardiovascular disorders. Furthermore, this invention addresses the disparate responsiveness of humans to antihypertensive monotherapy, based on age and/or ethnicity (Campo C, Segura J, Ruilope L M, J Clin Hypertens (Greenwich) 2002 January, 4(1):35-40). Finally, the choice of agents and their respective dosages in the combination regimen are designed to enhance tolerability by minimizing the risk of dose-dependent adverse effects associated with individual agents.

Numerous clinical studies have shown that lowering blood pressure in hypertensive patients reduces mortality and morbidity (Collins R, Peto R, MacMahon S, Hebert P, Fiebach N H, Eberlein K A, Godwin J, Qizilbash N, Taylor J O, Hennekens C H, Lancet 1990, 335(8693):827-38). Despite the availability and use of various classes of agents in the treatment of this medical condition, adequate control of blood pressure is not always achieved (Waeber B, Brunner H R, Am J Hypertens 1997, 10(7 Pt 2):131S-137S). Using a combination of agents is one way to achieve the desired therapeutic end-point. An arbitrary selection of antihypertensive agents of different classes for inclusion in a combination therapy regimen does not necessarily help achieve target levels of blood pressure in hypertensive mammals including humans (MacGregor G A, Markandu N D, Banks R A, Bayliss J, Roulston J E, Jones J C, Br Med J (Clin Res Ed), 284(6317): 693-6). Therefore, a need for further development of methods of treatment, combinations, and pharmaceutical compositions clearly exists.

Specifically, the present invention relates to pharmaceutical compositions comprising (i) an angiotensin receptor (Type 1, $AT_1$) blocker (ARB) selected from the group consisting of candesartan, eprosartan, irbesartan, losartan, olmesartan, saprisartan, tasosartan, telmisartan, valsartan, E-4177, SC-52458, and ZD8731, and pharmaceutically acceptable salts thereof; (ii) a calcium channel blocker (CCB) selected from the group consisting of amlodipine, felodipine, isradipine, lacidipine, nicardipine, nifedipine, niguldipine, niludipine, nimodipine, nisoldipine, nitrendipine, nivaldipine, ryosidine, anipamil, diltiazem, fendiline, flunarizine, gallopamil, mibefradil, prenylamine, tiapamil, and verapamil, and pharmaceutically acceptable salts thereof; and, (iii) a diuretic selected from the group consisting of bumetanide, ethacrynic acid, furosemide, torsemide, amiloride, spironolactone, triamterene, chlorothalidone, chlorothiazide, hydrochlorothiazide, hydroflumethiazide, methylchlorothiazide, metolazone, and dichlorphenamide, and pharmaceutically acceptable salts thereof where appropriate, i.e. if the diuretic compound is not already present as a pharmaceutically acceptable salt as e.g. in the case of hydrochlorothiazide; optionally in the presence of a pharmaceutically acceptable carrier. The invention further provides methods for treating hypertension and a variety of cardiovascular disorders enumerated below and their sequelae by administration of the pharmaceutical composition comprising (i) an angiotensin receptor blocker (ARB), (ii) a calcium channel blocker (CCB), (iii) and a diuretic to a mammal including humans.

Thus, the invention further relates to a pharmaceutical composition or a kit of parts, e.g. for the treatment or prevention of a condition or disease selected from the group consisting of hypertension, heart failure such as (acute and chronic) congestive heart failure, left ventricular dysfunction and hypertrophic cardiomyopathy, diabetic cardiac myopathy, supraventricular and ventricular arrhythmias, atrial fibrillation, atrial flutter, detrimental vascular remodeling, myocardial infarction and its sequelae, atherosclerosis, angina (whether unstable or stable), renal insufficiency (diabetic and non-diabetic), heart failure, angina pectoris, diabetes, secondary aldosteronism, primary and secondary pulmonary hypertension, renal failure conditions, such as diabetic nephropathy, glomerulonephritis, scleroderma, glomerular sclerosis, proteinuria of primary renal disease, and also renal vascular hypertension, diabetic retinopathy, the management of other vascular disorders, such as migraine, peripheral vascular disease, Raynaud's disease, luminal hyperplasia, cognitive dysfunction (such as Alzheimer's), glaucoma and stroke which composition (or kit of part) comprises (i) an ARB selected from the group consisting of candesartan, eprosartan, irbesartan, losartan, olmesartan, saprisartan, tasosartan, telmisartan, valsartan, E-4177, SC-52458, and ZD8731, or a pharmaceutically acceptable salt thereof; and (ii) a CCB selected from the group consisting of amlodipine, felodipine, isradipine, lacidipine, nicardipine, nifedipine, niguldipine, niludipine, nimodipine, nisoldipine, nitrendipine, nivaldipine, and ryosidine, which all belong to the group of dihydropyridines (DHPs) and the non-DHP CCBs anipamil, diltiazem, fendiline, flunarizine, gallopamil, mibefradil, prenylamine, tiapamil, and verapamil, or a pharmaceutically acceptable salt thereof; and (iii) a diuretic selected from the group consisting of bumetanide, ethacrynic acid, furosemide, torsemide, amiloride, spironolactone, triamterene, chlorothalidone, chlorothiazide, hydrochlorothiazide, hydroflumethiazide, methylchlorothiazide, metolazone, and dichlorphenamide, or, where appropriate, a pharmaceutically acceptable salt thereof and a pharmaceutically acceptable carrier.

A further aspect of the present invention is a method for the treatment or prevention of a condition or disease selected from the group consisting of hypertension, heart failure such as (acute and chronic) congestive heart failure, left ventricular dysfunction and hypertrophic cardiomyopathy, diabetic cardiac myopathy, supraventricular and ventricular arrhythmias, atrial fibrillation, atrial flutter, detrimental vascular remodeling, myocardial infarction and its sequelae, atherosclerosis, angina (whether unstable or stable), renal insufficiency (diabetic and non-diabetic), heart failure, angina pectoris, diabetes, secondary aldosteronism, primary and secondary pulmonary hypertension, renal failure conditions, such as diabetic nephropathy, glomerulonephritis, scleroderma, glomerular sclerosis, proteinuria of primary renal disease, and also renal vascular hypertension, diabetic retinopathy, the management of other vascular disorders, such as migraine, peripheral vascular disease, Raynaud's disease, luminal hyperplasia, cognitive dysfunction (such as Alzheimer's), glaucoma and stroke, comprising administering a therapeutically effective amount of combination of (i) an ARB selected from the group consisting of candesartan, eprosartan, irbesartan, losartan, olmesartan, saprisartan, tasosartan, telmisartan, valsartan, E-4177, SC-52458, and ZD8731, or a pharmaceutically acceptable salt thereof; and (ii) a CCB selected from the group consisting of amlodipine, felodipine, isradipine, lacidipine, nicardipine, nifedipine, niguldipine, niludipine, nimodipine, nisoldipine, nitrendipine, nivaldipine, and ryosidine, which all belong to the group of dihydropyridines (DHPs) and the non-DHP CCBs anipamil, diltiazem, fendiline, flunarizine, gallopamil, mibefradil, prenylamine, tiapamil, and verapamil, or a pharmaceutically acceptable salt thereof; and (iii) a diuretic selected from the group consisting of bumetanide, ethacrynic acid, furosemide, torsemide, amiloride, spironolactone, triamterene, chlorthalidone, chlorothiazide, hydrochlorothiazide, hydroflumethiazide, methylchlorothiazide, metolazone, and dichlorphenamide, or, where appropriate, a pharmaceutically acceptable salt thereof and a pharmaceutically acceptable carrier to a mammal in need of such treatment.

The invention also relates to combining separate pharmaceutical compositions in kit form. That is a kit combining two or three separate units: e.g. a pharmaceutical composition comprising an ARB, an pharmaceutical composition comprising a CCB, and a pharmaceutical composition comprising a diuretic; or a pharmaceutical composition comprising an ARB and a diuretic, and a pharmaceutical composition comprising a CCB; or a pharmaceutical composition comprising a CCB and a diuretic, and a pharmaceutical composition comprising an ARB. Although the kit form is particularly advantageous when the separate components must be administered in different dosage forms (e.g. parenteral valsartan formulation and oral amlodipine or hydrochlorothiazide formulations) or are administered at different dosage intervals, the administration of the single components of such a kit of parts may, without any restriction be effected simultaneously, sequentially or staggered with time.

In a preferred embodiment, the (commercial) product is a commercial package comprising as active ingredients the combination according to the present invention (in the form of two or three separate units of the components (i) to (iii)), together with instructions for its simultaneous, separate or sequential use, or any combination thereof, in the delay of progression or treatment of the diseases mentioned herein. A preferred commercial package, is where the ARB (i) and the diuretic (iii) are present in the form of Co-DIOVAN®, or where the ACE inhibitor (i), the CCB (ii) and the diuretic (iii) are present in the form of Co-DIOVAN® and NORVASC®.

The pharmaceutical preparations of the present invention are for enteral, such as oral, and also rectal or parenteral, administration to homeotherms, with the preparations comprising the pharmacological active compound either alone or together with customary pharmaceutical auxiliary substances. For example, the pharmaceutical preparations consist of from about 0.1% to 90%, preferably of from about 1% to about 80%, of the active compounds. Pharmaceutical preparations for enteral or parenteral administration are, for example, in unit dose forms, such as coated tablets, tablets, capsules or suppositories and also ampoules. These are prepared in a manner, which is known per se, for example using conventional mixing, granulation, coating, solubulizing or lyophilizing processes. Thus, pharmaceutical preparations for oral use can be obtained by combining the active compounds with solid excipients, if desired granulating a mixture which has been obtained, and, if required or necessary, processing the mixture or granulate into tablets or coated tablet cores after having added suitable auxiliary substances.

The dosage of the active compound can depend on a variety of factors, such as mode of administration, homeothermic species, age and/or individual condition. Preferred dosages for the active ingredients of the pharmaceutical combination according to the present invention are therapeutically effective dosages, especially those that are commercially available. Normally, in the case of oral administration, an approximate daily dose of from about 20 mg to about 900 mg of active agents, i.e. ARB plus CCB plus diuretic, is to be estimated e.g. for a patient of approximately 75 kg in weight.

In the present invention preferred ARBs are those agents that have been marketed, as e.g. valsartan and losartan. The same applies to the CCBs employed in the present invention, of which amlodipine and felodipine are preferred. The most preferred diuretic is hydrochlorothiazide (HCTZ).

Very surprisingly is the finding that, a combination of (i) an ARB, (ii) a CCB, and (iii) a diuretic and in particular a combination comprising valsartan, amlodipine and HCTZ achieves greater therapeutic effect than the administration of valsartan, amlodipine, or HCTZ alone or in a combination of two of these agents. Greater efficacy can also be documented as a prolonged duration of action. The duration of action can be monitored as either the time to return to baseline prior to the next dose or as the area under the curve (AUC) and is expressed as the product of the change in blood pressure in millimeters of mercury (change in mmHg) and the duration of the effect (minutes, hours or days). The aforementioned combination treatment also unexpectedly reduces blood pressure in hypertensive mammals in a smooth and sustained fashion. The trough:peak blood pressure ratio demonstrated by this combination is close to unity leading to a more homogenous blood pressure control during the inter-dosing period. The combined regimen is almost completely devoid of either orthostatic hypotension or first-dose hypotension, and incidences of rebound hypertension after cessation of treatment are very rare. It can be shown that combination therapy according to the invention results in lessening of pulse pressure in hypertensive mammals.

Furthermore, this combination therapy can ameliorate endothelial dysfunction and improve vascular compliance and distensibility in hypertensive mammals. It can also slow the progression of cardiac, renal and cerebral end-organ damage in these mammals. Further benefits are that lower doses of the individual drugs to be combined according to the present invention can be used to reduce the dosage, for example, that the dosages need not only often be smaller but are also applied less frequently, or can be used to diminish the incidence of side effects. Surprisingly, the combination of valsartan, amlodipine and HCTZ significantly reduce the incidences of peripheral edema relative to those observed in mammals treated with amlodipine alone. Also, the undesirable effects of HCTZ on serum lipids, glucose, and uric acid levels are surprisingly attenuated in mammals treated with the combined regimens of valsartan, amlodipine and HCTZ.

In particular the combined administration of valsartan or a pharmaceutically acceptable salt thereof, amlodipine or a pharmaceutically acceptable salt thereof, and HCTZ results in a significant response in a greater percentage of treated patients compared to monotherapy or combination therapy e.g. valsartan and HCTZ, that is, a greater responder rate results, regardless of the underlying etiology of the condition. This is in accordance with the desires and requirements of the patients to be treated. The combination treatment effectively lowers blood pressure in hypertensive patients in all age groups including pre and postmenopausal women. It can be shown that combination therapy with valsartan, amlodipine, and HCTZ results in a more effective antihypertensive therapy (whether for malignant, essential, reno-vascular, diabetic, isolated systolic, or other secondary type of hypertension) and lessening of pulse pressure through improved efficacy. The combination is also useful in the treatment or prevention of heart failure such as (acute and chronic) congestive heart failure, left ventricular dysfunction and hypertrophic cardiomyopathy, diabetic cardiac myopathy, supraventricular and ventricular arrhythmias, atrial fibrillation, atrial flutter or detrimental vascular remodeling. It can further be shown that a valsartan, amlodipine, and HCTZ combination therapy proves to be beneficial in the treatment and prevention of myocardial infarction and its sequelae. A valsartan, amlodipine, and HCTZ combination is also useful in treating atherosclerosis, angina (whether stable or unstable), renal insufficiency (diabetic and non-diabetic), peripheral vascular disease, cognitive dysfunction, and stroke. Furthermore, the improvement in endothelial function with the combination therapy using valsartan, amlodipine, and HCTZ provides benefit in diseases in which normal endothelial function is disrupted such as heart failure, angina pectoris and diabetes. Furthermore, the combination of the present invention may be used for the treatment or prevention of secondary aldosteronism, primary and secondary pulmonary hypertension, renal failure conditions, such as diabetic nephropathy, glomerulonephritis, scleroderma, glomerular sclerosis, proteinuria of primary renal disease, and also renal vascular hypertension, diabetic retinopathy, the management of other vascular disorders, such as migraine, peripheral vascular disease, Raynaud's disease, luminal hyperplasia, cognitive dysfunction (such as Alzheimer's), glaucoma and stroke. The combination regimen also surprisingly reduces the rate of progression of cardiac, renal and cerebral end-organ damage. By providing enhanced efficacy, safety and tolerability, the combination of drugs indicated in this invention also has the potential to promote patient compliance, a major consideration in the pharmacological treatment of hypertension.

The person skilled in the pertinent art is fully enabled to select a relevant test model to prove the efficacy of a combination of the present invention in the herein before and hereinafter indicated therapeutic indications.

The advantages of the present combinations are, for example, demonstrated in a clinical study or in the test procedure as essentially described hereinafter. Many clinical study protocols adapted to test our combinations are known by the person skilled in the art. An example of a clinical trial useful to demonstrate the unexpected advantages of our new combinations is described by Waeber B et al. (J Hypertens. 2001 November; 19(11):2097-104. The same protocol is performed with our preferred combinations such as a combination, preferably fixed-dose combination, of valsartan 80 mg, hydrochlorothiazide 12.5 mg, and amlodipine 5 mg. This protocol is hereby incorporated into the present application by reference to this publications.

Representative studies are carried out with a combination of valsartan, amlodipine, and HCTZ applying the following methodology. Drug efficacy is assessed in various animal models including the deoxycorticosterone acetate—salt rat (DOCA-salt) and the spontaneously hypertensive rat (SHR), either maintained on a normal salt diet or with salt loading (4-8% salt in rat chow or 1% NaCl as drinking water).

The DOCA-salt test model utilizes either an acute or chronic study protocol. An acute study procedure involves assessment of the effects of various test substances over a six-hour experimental period using rats with indwelling femoral arterial and venous catheters. The Acute Study Procedure evaluates test substances for their ability to reduce blood pressure during the established phase of DOCA-salt hypertension. In contrast, the Chronic Study Procedure assesses the ability of test substances to prevent or delay the rise in blood pressure during the development phase of DOCA-salt hypertension. Therefore, blood pressure will be monitored in the chronic study procedure by means of a radiotransmitter. The radiotransmitter is surgically implanted into the abdominal aorta of rats, prior to the initiation of DOCA-salt treatment and thus, prior to the induction of hypertension. Blood pressure is chronically monitored for periods of up 6 weeks (approximately one week prior to DOCA-salt administration and for 5 weeks thereafter).

Rats are anesthetized with 2-3% isoflurane in oxygen inhalant followed by Amytal sodium (amobarbital) 100 mg/kg, ip. The level of anesthesia is assessed by a steady rhythmic breathing pattern.

Acute Study Procedure:

Rats undergo a unilateral nephrectomy at the time of DOCA implantation. Hair is clipped on the left flank and the back of the neck and scrubbed with sterile alcohol swabs and povidone/iodine. During surgery rats are placed on a heating pad to maintain body temperature at 37° C.

A 20 mm incision is made through the skin and underlying muscle to expose the left kidney. The kidney is freed of surrounding tissue, exteriorized and two ligatures (3-0 silk) are tied securely around the renal artery and vein proximal to their juncture with the aorta. The renal artery and vein are then severed and the kidney removed. The muscle and skin wounds are closed with 4-0 silk suture and stainless steel wound clips, respectively. At the same time, a 15 mm incision is made on the back of the neck and a 3-week-release pellet (Innovative Research of America, Sarasota, Fla.) containing deoxycorticosterone acetate (100 mg/kg) is implanted subcutaneously. The wound is then closed with stainless-steel clips and both wounds are treated with povidone/iodine; the rats are given a post-surgical intramuscular injection of procaine penicillin G (100,000 U) and buprenorphine (0.05-0.1 mg/kg) s.c. The rats are immediately placed on 1% NaCl+0.2% KCl drinking water; this treatment continues for at least 3 weeks at which time the animals have become hypertensive and available for experimentation.

Forty-eight hours prior to experimentation, animals are anesthetized with isoflurane and catheters are implanted in the femoral artery and vein for measuring arterial pressure, collection of blood, and administration of test compounds. Rats are allowed to recover for 48 hours while tethered in a Plexiglas home cage, which also serves as the experimental chamber.

Chronic Study Procedure:

This procedure is the same as above except that rats are implanted with a radiotransmitter, 7-10 days prior to the unilateral nephrectomy and initiation of DOCA and salt. In addition, rats do not undergo surgery for placement of femoral arterial and venous catheters. Radiotransmitters are implanted as described in M. K. Bazil, C. Krulan and R. L. Webb. Telemetric monitoring of cardiovascular parameters in conscious spontaneously hypertensive rats. J. Cardiovasc. Pharmacol. 22: 897-905, 1993.

Protocols are then set-up on the computer for measurement of blood pressure, heart rate, etc, at predetermined time points. Baseline data is collected at various time points and over various time intervals. For example, baseline or pre-dose values usually consist of data collection and averaging over 3 consecutive, 24-hour time periods prior to drug administration.

Blood pressure, heart rate and activity are determined at various pre-selected time points before, during, and after drug administration. All measurements are performed in unrestrained and undisturbed animals. The maximum study time, determined by battery life, could be as long as nine months. For studies of this duration, rats are dosed orally (1-3 ml/kg vehicle), no more than twice daily or drug is administered via the drinking water or mixed with food. For studies of a shorter duration, that is, up to 8 weeks, drugs are given via subcutaneously implanted osmotic minipumps. Osmotic minipumps are selected based on drug delivery rate and time. Valsartan dosages range from 1 to 100 mg/kg/day, amlodipine dosages range from 1 to 75 mg/kg/day, and HCTZ dosages range from 1 to 75 mg/kg/day.

Additionally, SHR are utilized to study the effects of valsartan in combination with amlodipine, and HCTZ. The hypertensive background of the SHR is modified either by chronic salt loading in an effort to suppress the RAAS or chronic salt depletion to activate the RAAS in the SHR. These manipulations will be carried out to more extensively evaluate the efficacy of the various test substances. Experiments are performed in spontaneously hypertensive rats (SHR) supplied by Taconic Farms, Germantown, N.Y. (Tac:N(SHR) fBR). A radiotelemetric device (Data Sciences International, Inc., St. Paul, Minn.) is implanted into the lower abdominal aorta of all test animals between the ages of 14 to 16 weeks of age. All SHR are allowed to recover from the surgical implantation procedure for at least 2 weeks prior to the initiation of the experiments. Cardiovascular parameters are continuously monitored via the radiotransmitter and transmitted to a receiver where the digitized signal is then collected and stored using a computerized data acquisition system. Blood pressure (mean arterial, systolic and diastolic pressure) and heart rate are monitored in conscious, freely moving and undisturbed SHR in their home cages. The arterial blood pressure and heart rate are measured every 10 minutes for 10 seconds and recorded. Data reported for each rat represent the mean values averaged over a 24 hour period and are made up of the 144-10 minute samples collected each day. The baseline values for blood pressure and heart rate consist of the average of three consecutive 24 hour readings taken prior to initiating the drug treatments. All rats are individually housed in a temperature and humidity controlled room and are maintained on a 12 hour light dark cycle.

In addition to the cardiovascular parameters, weekly determinations of body weight also are recorded in all rats. Treatments are administered in the drinking water, via daily oral gavage or in osmotic minipumps as stated above. If given in drinking water, water consumption is measured five times per week. Valsartan, amlodipine, and HCTZ doses for individual rats are then calculated based on water consumption for each rat, the concentration of drug substance in the drinking water, and individual body weights. All drug solutions in the drinking water are made up fresh every three to four days. Typical dosages for valsartan in drinking water range from 1 to 100 mg/kg/day, dosages of amlodipine range from 1 to 75 mg/kg/day, and dosages of HCTZ range from 1 to 75 mg/kg/day. In most situations, a daily dose will not exceed 100 mg/kg/day when administered as the monotherapy. In combination, lower dosages of each agent are used and correspondingly, valsartan is given in the range of 1 to 30 mg/kg/day, and amlodipine and HCTZ are give in dosages below 50 mg/kg/day.

When drugs are administered by oral gavage, the dose of valsartan ranges from 1 to 50 mg/kg/day and that of amlodipine and HCTZ does not exceed 75 mg/kg/day, respectively.

Upon completion of the chronic studies, SHR or DOCA-salt rats are anesthetized, blood samples obtained for biochemical analysis and the heart rapidly removed. After separation and removal of the atrial appendages, left ventricle and left plus right ventricle (total) are weighed and recorded. Left ventricular and total ventricular mass are then normalized to body weight and reported.

Vascular function and structure are evaluated after treatment to assess the beneficial effects of the combination. SHR are studied according to the methods described by Intengan H D, Thibault G, Li J S, Schiffrin E L, Circulation 1999, 100 (22): 2267-2275. Similarly, the methodology for assessing vascular function in DOCA-salt rats is described in Intengan H D, Park J B, Schiffrin, E L, Hypertension, 1999, 34(4 Part 2): 907-913. Assessment of vascular compliance and distensibility following treatment with the combination regimen is performed according to the methods described by Ceiler D L, Nelissen-Vrancken H J, De Mey J G, Smits J F, J Cardiovasc Pharmacol 1998, 31(4):630-7. Amelioration of cardiac, renal, and cerebral injury secondary to hypertension is assessed after treatment with the combination regimen in salt-loaded stroke-prone spontaneously hypertensive rats according to the methods described by Nagura J, Yamamoto M, Hui C, Yasuda S, Hachisu M, Konno F, Clin Exp Pharmacol Physiol 1996, 23(3):229-35. Propensity of the combination therapy to elicit postural or orthostatic hypotension is assessed in SHRs by the methods described by Nabata H, Aono J, Ishizuka N, Sakai K, Arch Int Pharmacodyn Ther 1985, 277(1):104-18. Tendency to produce peripheral edema by the combination regimen was assessed by the methods described by Lacolley P, Poitevin P, Koen R, Levy B I, J Hypertens 1998, 16(3):349-55.

Valsartan is supplied in the form of suitable dosage unit form, for example, a capsule or tablet, and comprising a therapeutically effective amount, e.g. from about 20 to about 320 or 640 mg, of valsartan which may be applied to patients. The application of the active ingredient may occur up to three times a day, starting e.g. with a daily dose of 20 mg or 40 mg of valsartan, increasing via 80 mg daily and further to 160 mg daily up to 320 or 640 mg daily. Preferably, valsartan is applied once a day or twice a day in heart failure patients with a dose of 80 mg or 160 mg, respectively, each. Corresponding doses may be taken, for example, in the morning, at mid-day or in the evening. Preferred is q.d. or b.i.d. administration in heart failure.

In case of amlodipine, preferred dosage unit forms are, for example, tablets or capsules comprising e.g. from about 1 mg to about 60 mg, preferably 2.5 to 20 mg, more preferably between 2.5 and 10 mg daily when administered orally.

In case of HCTZ, preferred dosage unit forms are, for example, tablets or capsules comprising e.g. from about 5 mg to about 200 mg preferably from about 50 mg to about 150 mg, even more preferably from about 25 mg to about 100 mg and even more preferably from about 5 mg to about 25 mg, administered orally once a day.

An example of a preferred composition, comprises an amount of Valsartan between 60 and 100 mg e.g. 80 mg, an amount of amlodipine between 2 and 12 mg e.g. 2.5 or 5 mg and an amount of HCTZ between 8 and 16 mg e.g. 12.5 mg.

Another example of a preferred composition, comprises an amount of Valsartan between 140 and 180 mg e.g. 160 mg, an amount of amlodipine between 2 and 12 mg e.g. 2.5 or 5 or 10 mg and an amount of HCTZ between 8 and 16 mg e.g. 12.5 mg.

Another example of a preferred composition comprises an amount of Valsartan between 140 and 180 mg e.g. 160 mg, an amount of amlodipine between 4 and 12 mg e.g. 5 mg or 10 mg, and an amount of HCTZ between 20 and 30 mg e.g. 25 mg.

The combination of (i) an ARB, (ii) a CCB, and (iii) a diuretic may, according to the present invention be manufactured and administered in free or fixed dose combinations of the respective pharmaceutically active agents. It may be advantageous to begin the treatment with free combinations that allow an easy adjustment of the administered dose of each individual agent. When the ideal dose regimen, which generally is dependent on the specific condition of the individual to be treated, the individuals weight, other medication administered to the individual and the like, is reached, a fixed dose combination may be administered in case where an administration once a day or e.g. twice or three times daily is possible and a sufficient control of blood pressure is achieved.

Presently it is preferred to combine two of the components (i) to (iii) and administer the third separately at the same or at a different time.

Valsartan is being marketed under the trade name Diovan®. A combination of valsartan and HCTZ is being marketed under the trade name Co-Diovan® and amlodipine is being marketed under the trade name Norvasc®. All of these marketed products may be utilized in as such for combination therapy according to the present invention.

The following examples illustrate the invention described above and are not intended to restrict the scope of this invention in any way.

FORMULATION EXAMPLE 1

| | Composition and batch quantities for Diovan ® tablets | | | | | | | |
|---|---|---|---|---|---|---|---|---|
| | COMPOSITION PER UNIT (mg) | | | | QUANTITY PER BATCH[1] (kg) | | | |
| Components | 40 mg | 80 mg | 160 mg | 320 mg | 40 mg | 80 mg | 160 mg | 320 mg |
| Granulation | | | | | | | | |
| Diovan Drug Substance | 40.000 | 80.000 | 160.000 | 320.000 | 144.000 | 144.000 | 144.000 | 144.000 |
| Microcrystalline Cellulose(NF, Ph. Eur.) Avicel PH102 | 27.000 | 54.000 | 108.000 | 216.000 | 97.200 | 97.200 | 97.200 | 97.200 |
| Crospovidone (NF, Ph. Eur.) | 7.500 | 15.000 | 30.000 | 60.000 | 27.000 | 27.000 | 27.000 | 27.000 |
| Colloidal Anhydrous Silica (Ph. Eur.)/Colloidal silicon Dioxide (NF)/Aerosil 200 | 0.750 | 1.500 | 3.000 | 6.000 | 2.700 | 2.700 | 2.700 | 2.700 |
| Magnesium Stearate (NF, Ph. Eur.) | 1.500 | 3.000 | 6.000 | 12.000 | 5.400 | 5.400 | 5.400 | 5.400 |
| Blending | | | | | | | | |
| Magnesium Stearate (NF, Ph. Eur.) | 0.750 | 1.500 | 3.000 | 6.000 | 2.700 | 2.700 | 2.700 | 2.700 |
| Coating | | | | | | | | |
| DIOLACK Gelb F32892 | 2.800 | | | | 11.090[2] | | | |
| DIOLACK Blassrot F34899 | | 6.000 | | | | 12.420[3] | | |
| DIOLACK Hellbraun F33172 | | | 9.000 | | | | 9.720[4] | |
| DIOLACK Braun F16711 | | | | 16.000 | | | | 8.640[4] |
| Purified Water | | | | | 62.843 | 70.380 | 55.080 | 48.960 |
| Total Tablet/Batch Weight | 80.300 | 161.000 | 319.000 | 636.000 | 289.080 | 289.800 | 287.100 | 286.200 |

[1] A total of 2 subdivisions of granulation per batch
[2] A 10% excess of coating solution was manufactured to account for loss during coating.
[3] A 15% excess of coating solution was manufactured to account for loss during coating.
[4] A 20% excess of coating solution was manufactured to account for loss during coating.

| | | | | Composition of Diolack | | | |
|---|---|---|---|---|---|---|---|
| DIOLACK | HPMC USP/Ph. Eur (603) | PEG 8000 USP/Ph. Eur. | Titanium Dioxide (White) USP/Ph. Eur | Iron Oxide (Red) Ph. Fr./NF/ E172/CFR/ CI 77491 | Iron Oxide (Yellow) Ph. Fr./NF/ E172/CFR/ CI 77492 | Iron Oxide (Brown) Mixture of iron oxide red & black | Iron Oxide (Black) E172/CFR/ CI 77499 |
| Gelb F32892 | 80.00% | 4.00% | 13.48% | 0.01% | 2.50% | — | 0.01% |
| Blassrot F34899 | 80.00% | 4.00% | 15.50% | 0.40% | 0.10% | — | — |
| Hellbraun F33172 | 80.00% | 4.00% | 9.34% | 0.25% | 6.40% | — | 0.01% |
| Braun F16711 | 80.00% | 4.00% | 14.00% | 0.50% | 0.50% | 0.50% | 0.50% |

A mixture of Diovan drug substance, microcrystalline cellulose, crospovidone, part of the colloidal anhydrous silica/colloidal silicon dioxide/Aerosile 200, silicon dioxide and magnesium stearate is premixed in a diffusion mixer and then sieved through a screening mill. The resulting mixture is again pre-mixed in a diffusion mixer, compacted in a roller compacter and then sieved through a screening mill. To the resulting mixture, the rest of the colloidal anhydrous silica/colloidal silicon dioxide/Aerosile 200 are added and the final blend is made in a diffusion mixer. The whole mixture is compressed in a rotary tabletting machine and the tablets are coated with a film by using the appropriate composition of Diolack in a perforated pan.

FORMULATION EXAMPLE 2

| Components | COMPOSITION PER UNIT (mg) | COMPOSITION PER UNIT (mg) | COMPOSITION PER UNIT (mg) |
|---|---|---|---|
| Granulation | | | |
| Diovan Drug Substance | 80.000 | 160.000 | 160.00 |
| Esidrex Drug Substance (micro) | 12.500 | 12.500 | 25.00 |
| Microcrystalline Cellulose (NF, Ph. Eur.)/Avicel PH 102 | 31.500 | 75.500 | 63.00 |
| Crospovidone (NF, Ph. Eur.) | 20.000 | 40.000 | 40.00 |
| Colloidal Anhydrous Silica (Ph. Eur.)/Colloidal Silicon Dioxide (NF)/Aerosil 200 | 1.500 | 3.00 | 3.00 |
| Magnesium Stearate (NF, Ph. Eur.) | 3.000 | 6.000 | 6.00 |
| Blending | | | |
| Magnesium Stearate, NF, Ph. Eur. | 1.500 | 3.000 | 3.00 |
| Coating | | | |
| Opadry Black OOF17713 | — | — | 0.096 |
| Opadry Red OOF15613 | — | — | 0.762 |
| Opadry Yellow OOF12951 | — | — | 3.808 |
| Opadry White OOF18296 | — | — | 5.334 |
| Hydroxy propyl Methylcellulose | 2.76 | 5.510 | — |
| Iron Oxide Yellow | 0.025 | — | — |
| Iron Oxide Red | 0.025 | 0.750 | — |
| Polyethylene Glycol 8000 | 0.50 | 1.000 | — |
| Talc | 2.000 | 3.990 | — |
| Titanium Dioxide | 0.70 | 0.750 | — |
| Total Tablet/Batch Weight | 156.000 | 312.000 | 310.00 |

| | | | | Composition of Opadry | | | |
|---|---|---|---|---|---|---|---|
| OPADRY | HPMC USP/Ph. Eur (603) | PEG 4000 USP/Ph. Eur. | Talc USP/Ph. Eur | Titanium Dioxide USP/Ph. Eur (White) | Iron Oxide (Red) Ph. Fr./NF/ E172/CFR/ CI 77491 | Iron Oxide (Yellow) Ph. Fr./NF/ E172/CFR/ CI 77492 | IronOxide (Black) E172/CFR/ CI 77499 |
| Opadry White OOF18296* | 71.4% | 7.15% | 7.15% | 14.3% | — | — | — |
| Opadry Red OOF15613* | 71.4% | 7.15% | 7.15% | — | 14.3% | — | — |
| Opadry Red OOF15613* | 71.4% | 7.15% | 7.15% | — | — | 14.3% | — |
| Opadry Black OOF17713* | 71.4% | 7.15% | 7.15% | — | — | — | 14.3% |

A mixture of Diovan drug substance, Esidrex drug substance (micro), microcrystalline cellulose, crospovidone, colloidal anhydrous silica/Aerosil 200 and part of the magnesium stearate is premixed in a diffusion mixer and then sieve through a screening mill. The resulting mixture is again premixed in a diffusion mixer, compacted in a roller compacter and then sieved through a screening mill. The final blend is made in a diffusion mixer under addition of the remaining part of the magnesium stearate, which is hand screened before. The whole mixture is compressed in a rotary tabletting machine and the tablets are coated with a film by using the appropriate composition of Opadry in a perforated pan.

FORMULATION EXAMPLE 3

Composition and quantities for a combination of valsartan and amlodipine

| Components | COMPOSITION PER UNIT (mg) | COMPOSITION (%) |
|---|---|---|
| Diovan Drug Substance | 80.00 | 43.02 |
| Amlodipine Drug Substance | 6.94 | 3.73 |
| Avicel 102 (I) | 54.00 | 29.04 |
| Avicel 102 (II) | 20.00 | 10.76 |
| Crospovidone (I) | 15.00 | 8.07 |
| Crospovidone (II) | 4.0 | 2.15 |
| Cab-O-Sil | 1.50 | 0.81 |
| Magnesium Stearate (I) | 3.00 | 1.61 |
| Magnesium Stearate (II) | 1.50 | 0.81 |
| | 185.94 | 100.00 |

The tablet is manufactured e.g essentially as described in Formulation Example 1.

What is claimed is:

1. A pharmaceutical composition comprising
   (i) a pharmaceutically effective amount of valsartan or a pharmaceutically acceptable salt thereof,
   (ii) a pharmaceutically effective amount of amlodipine or a pharmaceutically acceptable salt thereof, and
   (iii) a pharmaceutically effective amount of hydrochlorothiazide or a pharmaceutically acceptable salt thereof.

2. The pharmaceutical composition of claim 1, wherein said composition is a fixed dose combination.

3. The pharmaceutical composition of claim 2, wherein said fixed dose combination is in the form of a capsule or tablet.

4. The pharmaceutical composition of claim 1, 2 or 3, wherein valsartan is present in an amount from about 20 to about 640 mg; amlodipine is present in an amount from about 1 mg to about 60 mg; and hydrochlorothiazide is present in an amount from about 5 mg to about 200 mg.

5. The pharmaceutical composition of claim 1, 2 or 3, wherein valsartan is present in an amount from about 40 to about 320 mg; amlodipine is present in an amount from about 2.5 mg to about 10 mg; and hydrochlorothiazide is present in an amount from about 5 mg to about 25 mg.

6. The pharmaceutical composition of claim 1, 2 or 3, wherein valsartan is present in an amount from about 160 to about 320 mg; amlodipine is present in an amount from about 5 to about 10 mg; and hydrochlorothiazide is present in an amount from about 12.5 to about 25 mg.

7. The pharmaceutical composition of claim 1, 2 or 3, wherein valsartan is present in an amount of about 160 mg; amlodipine is present in an amount of about 10 mg; and hydrochlorothiazide is present in an amount of about 12.5 mg.

8. The pharmaceutical composition of claim 1, 2 or 3, wherein valsartan is present in an amount of about 160 mg; amlodipine is present in an amount of about 10 mg; and hydrochlorothiazide is present in an amount of about 25 mg.

9. The pharmaceutical composition of claim 1, 2 or 3, wherein valsartan is present in an amount of about 320 mg; amlodipine is present in an amount of about 10 mg; and hydrochlorothiazide is present in an amount of about 25 mg.

10. The pharmaceutical composition of claim 1, 2 or 3, wherein valsartan is present in an amount of about 160 mg; amlodipine is present in an amount of about 5 mg; and hydrochlorothiazide is present in an amount of about 12.5 mg.

11. The pharmaceutical composition of claim 1, 2 or 3, wherein valsartan is present in an amount of about 160 mg; amlodipine is present in an amount of about 5 mg; and hydrochlorothiazide is present in an amount of about 25 mg.

12. The pharmaceutical composition of claim 7, wherein amlodipine is present in a pharmaceutically acceptable besylate salt form.

13. The pharmaceutical composition of claim 8, wherein amlodipine is present in a pharmaceutically acceptable besylate salt form.

14. The pharmaceutical composition of claim 9, wherein amlodipine is present in a pharmaceutically acceptable besylate salt form.

15. The pharmaceutical composition of claim 10, wherein amlodipine is present in a pharmaceutically acceptable besylate salt form.

16. The pharmaceutical composition of claim 11, wherein amlodipine is present in a pharmaceutically acceptable besylate salt form.

17. A kit comprising:
   (i) a pharmaceutically acceptable dose unit comprising a pharmaceutically effective amount of valsartan or a pharmaceutically acceptable salt thereof,
   (ii) a pharmaceutically acceptable dose unit comprising a pharmaceutically effective amount of amlodipine or a pharmaceutically acceptable salt thereof, and
   (iii) a pharmaceutically acceptable dose unit comprising a pharmaceutically effective amount of hydrochlorothiazide or a pharmaceutically acceptable salt thereof,
   wherein two of said pharmaceutically acceptable dose units can optionally take the form of a single pharmaceutically acceptable dose unit.

18. The kit of claim 17 wherein amlodipine is present in a pharmaceutically acceptable besylate salt form.

19. The kit of claim 17 or 18, wherein the amount of valsartan present in one of said dose units is from about 20 to about 640 mg; the amount of amlodipine present in one of said dose units is from about 1 mg to about 60 mg; and the amount of hydrochlorothiazide present in one of said dose units is from about 5 mg to about 200 mg.

20. The kit of claim 17 or 18, wherein the amount of valsartan present in one of said dose units is from about 40 to about 320 mg; the amount of amlodipine present in one of said dose units is from about 2.5 mg to about 10 mg; and the amount of hydrochlorothiazide present in one of said dose units is from about 5 mg to about 25 mg.

21. The kit of claim 17 or 18, wherein the amount of valsartan present in one of said dose units is from about 160 to about 320 mg; the amount of amlodipine present in one of said dose units is from about 5 to about 10 mg; and the amount of hydrochlorothiazide present in one of said dose units is from about 12.5 to about 25 mg.

22. The kit of claim 17 or 18, wherein the amount of valsartan present in one of said dose units is about 160 mg; the amount of amlodipine present in one of said dose units is about 10 mg; and the amount of hydrochlorothiazide present in one of said dose units is about 12.5 mg.

23. The kit of claim 17 or 18, wherein the amount of valsartan present in one of said dose units is about 160 mg; the amount of amlodipine present in one of said dose units is about 10 mg; and the amount of hydrochlorothiazide present in one of said dose units is about 25 mg.

24. The kit of claim 17 or 18, wherein the amount of valsartan present in one of said dose units is about 320 mg; the amount of amlodipine present in one of said dose units is about 10 mg; and the amount of hydrochlorothiazide present in one of said dose units is about 25 mg.

25. The kit of claim 17 or 18, wherein the amount of valsartan present in one of said dose units is about 160 mg; the amount of amlodipine present in one of said dose units is about 5 mg; and the amount of hydrochlorothiazide present in one of said dose units is about 12.5 mg.

26. The kit of claim 17 or 18, wherein the amount of valsartan present in one of said dose units is about 160 mg; the amount of amlodipine present in one of said dose units is about 5 mg; and the amount of hydrochlorothiazide present in one of said dose units is about 25 mg.

27. The kit of claim 17 or 18 further comprising a set of instructions, wherein said instructions provide guidance on the use of said dose units for either:

(A) the treatment of or delaying the onset of a condition or disease selected from the group consisting of hypertension, peripheral edema, heart failure, congestive heart failure, left ventricular dysfunction, hypertrophic cardiomyopathy, diabetic cardiac myopathy, supraventricular arrhythmia, ventricular arrhythmia, atrial fibrillation, atrial flutter, detrimental vascular remodeling, myocardial infarction, sequelae of myocardial infarction, atherosclerosis, angina, renal insufficiency, angina pectoris, diabetes, secondary aldosteronism, pulmonary hypertension, and renal failure; or (B) the management of a condition or disease selected from the group consisting of migraine, peripheral vascular disease, Raynaud's disease, luminal hyperplasia, cognitive dysfunction, glaucoma and stroke.

28. The kit of claim 27, wherein said instructions provide guidance on the use of said dose units for the treatment of or delaying the onset of a condition or disease selected from the group consisting of hypertension and peripheral edema.

29. The kit of claim 28, wherein said instructions provide guidance on the use of said dose units for the treatment of or delaying the onset of hypertension.

30. The kit of claim 28, wherein said instructions provide guidance on the use of said dose units for the treatment of or delaying the onset of peripheral edema.

* * * * *